United States Patent [19]

Fuchikami et al.

[11] Patent Number: 5,151,535

[45] Date of Patent: Sep. 29, 1992

[54] FLUORINE-CONTAINING α,β-BIFUNCTIONAL COMPOUNDS AND PROCESS FOR THEIR PRODUCTION

[75] Inventors: Takamasa Fuchikami; Hisao Urata, both of Sagamihara, Japan

[73] Assignee: Sagami Chemical Research Center, Tokyo, Japan

[21] Appl. No.: 472,864

[22] Filed: Jan. 31, 1990

[30] Foreign Application Priority Data

Feb. 16, 1989 [JP]  Japan .................................. 1-35033
Feb. 16, 1989 [JP]  Japan .................................. 1-35034
May 2, 1989 [JP]  Japan .................................. 1-112081

[51] Int. Cl.$^5$ ............................................. C07C 53/21
[52] U.S. Cl. ..................................... 554/226; 554/231
[58] Field of Search ...................... 260/408; 562/596; 560/192, 227

[56] References Cited

U.S. PATENT DOCUMENTS 3,525,678 8/1970 Kim et al. ......................... 204/158
3,816,495 6/1974 Middleton ......................... 260/453

FOREIGN PATENT DOCUMENTS 352718 1/1990 European Pat. Off. ............ 260/408

OTHER PUBLICATIONS

Chemical Abstracts, vol. 60, #13, 1964, 15720g.
Lack et al, Journal of the American Chemical Society, vol. 90, #25, pp. 7001–7007, 1968.
Re et al, Chemical Abstracts, vol. 110, #24, p. 62, 1989.
Patent Abstracts of Japan, unexamined applications, C section, vol. 6, No. 186, Sep. 22, 1982 The Patent Office Japanese Government p. 73 C 126 *Kokai-No. 57-99 551 (Asahi Glass K.K.)*.

*Primary Examiner*—Paul F. Shaver
*Assistant Examiner*—D. D. Carr
*Attorney, Agent, or Firm*—Oblon, Spivak, McClelland, Maier & Neustadt

[57] ABSTRACT

A fluorine-containing α,ω-bifunctional compound having the formula:

$$R^1CHCH_2(CF_2)_nCH_2CHR^2 \quad (I)$$
$$\;\;\;|\qquad\qquad\qquad\quad\;\;|$$
$$\;\;\;X\qquad\qquad\qquad\quad\;\;X$$

wherein each of $R^1$ and $R^2$ independently is a hydrogen atom, an alkyl group or an aralkyl group; X is —COOH, —COOR$^3$, —COY or —NCO, wherein $R^3$ is an alkyl group or an aralkyl group and Y is a halogen atom or $N_3$; and n is an integer of at least 1 provided that when X is —COOH, n is an integer of at least 4.

1 Claim, No Drawings

FLUORINE-CONTAINING α,β-BIFUNCTIONAL COMPOUNDS AND PROCESS FOR THEIR PRODUCTION

The present invention relates to fluorine-containing α,ω-bifunctional compounds useful as starting materials for fluorine-containing polymers and a process for their production.

Fluorine-containing polymers are widely used for e.g. fiber-treating agents, optical fiber sheath materials, gas permeable membranes, gas separating agents or photoresists by virtue of their water and oil repellency, chemical resistance, weather and light resistance, heat resistance and low refractive index (e.g R & D Report No. 16, Most Advanced Applied Technology of Fluorine Compounds, C. M. C (1981)). However, most of them contain fluorine atoms on their polymer side chains, and those containing fluorine atoms in the polymer main chains are rather limited, for lack of a suitable method for the production of the materials for such polymers.

The fluorine-containing α,ω-bifunctional compounds of the present invention can be led to polyesters or polyamides containing fluorine atoms in their main chains.

For the production of fluorine-containing α,ω-dicarboxylic acids, there have been known (1) a method for producing 3,3,4,4-tetrafluoro-1,6-hexanedioic acid by decomposing 4,4,5,5-tetrafluoro-1-cyclohexene with ozone (Du pont, U.S. Pat. No. 2,871,260 (1959)), (2) a method for producing an α,ω-dicarboxylic acid by oxidizing a fluorine-containing α,ω-diol with chromic acid/sulfuric acid (T. Takakura et al, J. Fluorine Chem., 41, 173 (1988)), and (3) a method wherein 1,2-iodo-1,1,2,2-tetrafluoroethane and acrylonitrile are reacted for a long period of time under irradiation with a mercury lamp to obtain 2,7-iodo-4,4,5,5-tetrafluoro-1,8octanedinitrile, which is reduced by zinc/sulfuric acid to obtain 4,4,5,5-tetrafluro-1,8-octanedinitrile, which is then hydrolyzed to 4,4,5,5-tetrafluoro-1,8-octanedioic acid (M. W. Bloechl, French Patent 1404744 (1965)).

It has been reported that the fluorine-containing α,ω-dicarboxylic acid produced by the method (1) or (2) can be converted to an isocyanate, and then a fluorine-containing polyurethane useful as an antithrombotic agent, can be produced therefrom (M. Kato et al, Progress in Artificial Organs., 2, 858 (1983)). However, the dicarboxylic acid produced by such a method is limited to the one wherein only one methylene chain is present between the difluoromethylene group and each carboxyl group. Heretofore, fluorine-containing α,ω-bifunctional compounds wherein only one methylene chain is present between the difluoromethylene group and each functional group, have been known (T. Takakura et al, J. Fluorine Chem., 41, 173 (1988)). However, such compounds are easily decomposed under a basic condition and thus have a drawback that they are inferior in the chemical resistance. Therefore, they require a careful handling. It is also well known to those skilled in the art that they are inferior in the weather resistance and durability. Further, the dicarboxylic acids as their starting materials are also inferior in the chemical resistance and require many steps for their synthesis. On the other hand, the 4,4,5,5-tetrafluoro-1,8-octanedioic acid produced by the method (3) has only four fluorine atoms per molecule, whereby the characteristic effects by the introduction of fluorine atoms, such as the above-mentioned water and oil repellency, are not adequate (see the Reference Examples given hereinafter). Further, many steps are required for its production, and it is necessary to use an apparatus for photo reaction. Besides, it has a drawback that the yield is low.

Under these circumstances, it is an object of the present invention to overcome the above-mentioned various drawbacks of the prior art and to provide novel fluorine-containing α,ω-bifunctional compounds which have excellent water and oil repellency and chemical resistance and yet adequate fluorine-introducing effects.

Another object of the present invention is t provide an efficient and economical process for the production of such fluorine-containing α,ω-bifunctional compounds.

The present invention provides a fluorine-containing α,ω-bifunctional compound having the formula:

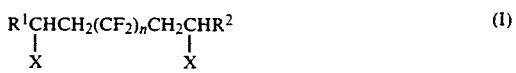

(I)

wherein each of $R^1$ and $R^2$ independently is a hydrogen atom, an alkyl group or an aralkyl group; X is —COOH, —COOR$^3$, COY or —NCO, wherein $R^3$ is an alkyl group or an aralkyl group and Y is a halogen atom or N$_3$; and n is an integer of at least 1 provided that when X is —COOH, n is an integer of at least 4.

The present invention also provides a process for producing the compound of the formula I, which comprises:

(i) reacting a fluorine-containing α,ω-diiodoalkane of the formula:

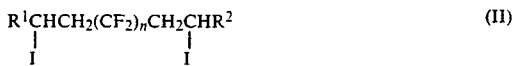

(II)

wherein $R^1$ and $R^2$ are as defined above, with an alcohol of the formula:

(III)

wherein $R^3$ is as defined above, and carbon monooxide in the presence of a Group VIII transition metal catalyst and a base to form compound of the formula I wherein X is —COOR$^3$ wherein $R^3$ is as defined above;

(ii) reacting the compound of the formula II with carbon monooxide and water in the presence of a Group VIII transition metal catalyst and a base to form a compound of the formula I wherein X is —COOH;

(iii) reacting the compound of the formula I wherein X is —COOH with a halogenating agent to form a compound atom;

(iv) reacting the compound of the formula I wherein X is —COY wherein Y is a halogen atom, with an alkali metal salt of hydrazoic acid or with hydrazoic acid in the presence of a base, to form a compound of the formula I wherein X is —COY wherein Y is N$_3$; or (v) subjecting the compound of the formula I wherein X is —COY wherein Y is N$_3$, to Curtius rearrangement, to form a compound of the formula I wherein X is —NCO.

Now, the present invention will be described in detail with reference to the preferred embodiments.

Referring to the compound of the formula I, the alkyl group for each of $R^1$, $R^2$ and $R^3$ is preferably an alkyl group having from 1 to 10 carbon atoms, which may have substituents. As such an alkyl group, a methyl group, an ethyl group, a propyl group, a 3,3,3-trifluoropropyl group, a butyl group, a hexyl group, a cyclohexyl group, an octyl group or a decyl group, may be mentioned. The aralkyl group for each of $R^1$, $R^2$ and $R^3$ is preferably an aralkyl group having from 7 to 10 carbon atoms which may have substituents. As such an aralkyl group, a benzyl group, a pentafluorobenzyl group or a phenethyl group may be mentioned.

Among the compounds of the present invention, those having the formula I wherein X is $-COOR^3$ are novel fluorine-containing $\alpha,\omega$-dicarboxylic acid diesters which have low refractive indices by themselves and yet can readily be formed into fluorine-containing polymers such as fluorine-containing polyesters or polyamides.

As mentioned above, such a diester i.e. a compound of the formula I wherein X is $-COOR^3$, is produced by reacting a fluorine-containing $\alpha,\omega$-diiodoalkane of the formula II with an alcohol of the formula III and carbon monooxide.

As the alkyl group in the starting material of the formula II in the present invention, it is preferred to employ an alkyl group having from 1 to 10 carbon atoms, which may have substituents. Such an alkyl group includes, for example, a methyl group, an ethyl group, a propyl group, a 3,3,3-trifluoropropyl group, a butyl group, a hexyl group, a cyclohexyl group, an octyl group and a decyl group. As the aralkyl group, it is preferred to employ an aralkyl group having from 7 to 10 carbon atoms, which may have substituents. Such an aralkyl group includes, for example, a benzyl group, a pentafluorobenzyl group and a phenethyl group.

The fluorine-containing $\alpha,\omega$-diiodoalkane of the formula II in the present invention may be commercially available. However, the one wherein $R^1$ and $R^2$ are the same, can simply, safely and advantageously be produced by reacting an $\alpha,\omega$-diiodopolyfluoroalkane of the formula:

$$I(CF_2)_nI \qquad (IV)$$

wherein n is as defined above, with an olefin of the formula:

$$CH_2=CHR^1 \qquad (V)$$

wherein $R^1$ is as defined above, in the presence of a Group VIII transition metal catalyst (see the Reference Examples give hereinafter). The $\alpha,\omega$-diiodopolyfluoroalkane of the formula IV is commercially available, and the olefin of the formula V is also commercially available. The olefin is used in an amount of 2 equivalents, or in an excess amount, relative to the $\alpha,\omega$-diiodoperfluoroalkane of the formula IV. As the Group VIII transition metal catalyst, a metal, a metal salt, a metal complex compound, an organometallic complex having carbon monooxide as a ligand, an organometallic complex having a halogen atom as a ligand, an organometallic complex having a tertiary phosphine as a ligand, an organometallic complex having an olefin or an acetylene as a ligand, of iron, ruthenium, osmium, cobalt, rhodium, iridium, nickel, palladium or platinum, or such a Group VIII transition metal compound supported on a carrier such as silica gel or alumina, may be employed. Suitable catalysts include, for example, iron carbonyl, ruthenium carbonyl, osmium carbonyl, cobalt carbonyl, rhodium carbonyl, nickel carbonyl, iron chloride, cobalt chloride, ruthenium chloride, rhodium chloride, nickel chloride, palladium chloride, platinum chloride, dichlorobis(triphenylphosphine)nickel, dichlorobis(triphenylphosphine)palladium, dichloro[1,2-bis(diphenylphosphino)ethane]palladium, dichloro[1,3-bis(diphenylphosphino)propane]palladium, dichloro[1,4-bis)diphenylphosphino)butane]palladium, dichloro[1,1'-bis(diphenylphosphino)ferrocene]palladium, dichlorobis(diphenylmethylphosphine)palladium, dichlorobis(triphenylphosphine)platinum, bis(cyclooctadiene)nickel, dichloro(cyclooctadiene)palladium, tetrakis(triphenylphosphine)nickel, chlorotris(triphenylphosphine)rhodium, chlorotris(triphenylphosphine)iridium, chlorocarbonylbis(triphenylphosphine)rhodium, chlorocarbonylbis(triphenylphosphine)iridium, tetrakis(triphenylphosphine)palladium, and tetrakis(triphenylphosphine)platinum. The amount of the Group VIII transition metal catalyst is suitably selected within a range of from 1/10,000 to ½ equivalent relative to the $\alpha,\omega$-diiodoperfluoroalkane of the formula V. An amount within a range of from 1/500 to ⅓ is preferred. If desired, an amine such as pyridine, triethylamine, diethylamine or ethanol amine, may be added as a cocatalyst. The reaction proceeds smoothly at a temperature of from 0 to 150° C. The reaction may be conducted in the absence of a solvent. However, if desired, a solvent inert to the reaction may be employed.

The alcohol of the formula III to be used in the present invention, includes methanol, ethanol, linear and cyclic primary and secondary propanols, butanols, pentanols and hexanols which may be branched, benzyl alcohol and phenethyl alcohol. The alcohol of the formula III is usually used in an excess amount relative to the compound of the formula II, and it may also be used as a solvent.

The reaction (i) of the present invention is conducted in an atmosphere of carbon monooxide, which may be diluted by an inert gas which does not affect the reaction. The reaction proceeds efficiently under a carbon monooxide partial pressure of at most 50 atm. However, if desired, a higher pressure may be employed.

It is essential to conduct the reaction (i) in the presence of a Group VIII transition metal catalyst. As the Group VIII transition metal catalyst which can be used here, a metal, a metal salt, a metal complex compound, an organometallic complex having carbon monooxide as a ligand, an organometallic complex having a halogen atom as a ligand, an organometallic complex having a tertiary phosphine as a ligand or an organometallic complex having an olefin or an acetylene as a ligand, of iron, cobalt, ruthenium, osmium, rhodium, iridium, nickel, palladium or platinum, or such a Group VIII transition metal compound supported on a carrier such as silica gel or alumina, may be employed. Suitable catalysts include, for examples, iron carbonyl, ruthenium carbonyl, osmium carbonyl, cobalt carbonyl, rhodium carbonyl, nickel carbonyl, iron chloride, cobalt chloride, ruthenium chloride, rhodium chloride, nickel chloride, palladium chloride, platinum chloride, dichlorobis(triphenylphosphine)nickel, dichlorobis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocene]palladium, dichlorobis(diphenylmethylphosphine)palladium, dichlorobis(triphenylphosphine)platinum, bis(cyclooctadiene)nickel, dichloro(cyclooctadiene)palladium, tetrakis(triphenylphosphine)nickel, chlorotris(triphenylphosphine)rhodium, chlorotris(triphenylphosphine)iridium, chlorocarbonylbis(triphenylphosphine)rhodium, chlorocarbonylbis(triphenylphosphine)iridium, tetrakis(triphenylphosphine)palladium, tetrakis(triphenylphosphine)platinum, and dichlorotris(triphenylphosphine)ruthenium. The amount of the Group VIII transition metal catalyst is suitably selected within a range of from 1/10,000 to ½ equivalent relative to the fluorine-containing α,ω-diiodoalkane of the formula II. An amount within a range of from 1/500 to ½ equivalent is preferred.

It is essential to conduct the reaction (i) in the presence of a base. As such a base, a hydroxide of an alkali metal or an alkaline earth metal, an inorganic salt such as a carbonate, a fluoride or an oxide, or an organic base such as triethylamine or pyridine, may be mentioned. The base is used preferably at least 1 equivalent relative to the compound of the formula II.

To conduct the reaction (i), a solvent inert to the reaction may be employed. For example, an aliphatic hydrocarbon solvent such as hexane, heptane, octane, cyclohexane or cyclooctane, an aromatic hydrocarbon solvent such as benzene, toluene or xylene, or a polar solvent such as acetone, chloroform, ethyl ether, tetrahydrofuran, dioxane, t-butyl alcohol or t-amyl alcohol, may be mentioned.

In a case where the solvent forms two liquid phases or when the base is hardly soluble in the solvent, a phase transfer catalyst such as a quaternary ammonium salt, may be added as the case requires.

The reaction temperature can suitably be selected within a temperature range of from 20 to 200° C. However, a temperature within a range of from 50 to 150° C. is preferred.

Now, referring to the reaction (ii), a fluorine-containing α,ω-dicarboxylic acid of the formula I wherein X is —COOH is prepared by reacting the compound of the formula II with carbon monooxide and water in the presence of a Group VIII transition metal catalyst and a base.

The compound of the formula II is as defined above with respect to the reaction (i). Likewise, the Group VIII transition metal catalyst and the base used in this reaction (ii) are as defined above with respect to the reaction (i).

In the reaction (ii), water is used usually in an excess amount, preferably from 2 to 200 times, relative to the compound of the formula II.

This reaction is conducted in an atmosphere of carbon monooxide, which may be diluted with an inert gas which does not affect the reaction. The reaction proceeds efficiently under a carbon monooxide partial pressure of at most 50 atm. If desired, however, a higher pressure may be employed.

The amount of the Group VIII transition metal catalyst can be selected suitably within a range of from 1/10,000 to ½ equivalent relative to the fluorine-containing α,ω-diiodoalkane of the formula II. An amount within a range of from 1/500 to ⅓ is preferred.

The base is used preferably in an amount of at least equivalent relative to the compound of the formula II.

To conduct the reaction (ii), a solvent which is inert to the reaction, may be used. As such a solvent, those mentioned above with respect to the reaction (i) may be employed.

In a case where the solvent forms two liquid phases or when the base is hardly soluble in the solvent, a phase transfer catalyst such as a quaternary ammonium salt may be added as the case requires.

The reaction temperature can be selected suitably within a temperature range of from 20 to 200° C. A temperature within a range of from 50 to 150° C. is preferred.

Now, referring to the reaction (iii), a fluorine-containing α,ω-dicarbonyl dihalide i.e. a compound of the formula I wherein X is COY wherein Y is a halogen atom, is prepared by reacting the fluorine-containing α,ω-dicarboxylic acid i.e. the compound of the formula I wherein X is —COOH, with a halogenating agent.

The halogenating agent may be any agent which is commonly employed for converting a carboxylic acid to an acid halide. For example, thionyl chloride, phosphorus pentachloride, silicon tetrachloride, oxalyl halide or phosphorus tribromide may suitably be used. It is used usually in an amount of 2 equivalents or in an excess amount relative to the compound of the formula I wherein X is —COOH. The reaction proceeds in the absence of any solvent. However, a solvent which is inert to the reaction may be employed, if desired.

The reaction proceeds smoothly within a temperature range of from room temperature to 150° C.

Now, referring to the reaction (iv) a fluorine-containing α,ω-dicarbonyl diazide i.e. a compound of the formula I wherein X is —CON$_3$, is prepared by reacting the fluorine-containing α,ω-dicarbonyl dihalide i.e. the compound of the formula I wherein X is —COY wherein Y is a halogen atom, with an alkali metal salt of hydrazoic acid or with hydrazoic acid in the presence of a base. Hydrazoic acid or the alkali metal salt of hydrazoic acid is used usually from 2 equivalent to an excess amount relative to the compound of the formula I wherein X is —COY wherein Y is a halogen atom.

As the base, an organic base such as pyridine or triethylamine, or an inorganic base such as potassium carbonate may suitably be used. The base is used usually from 2 equivalent to an excess amount.

The reaction is preferably conducted in a solvent. A solvent inert to the reaction, such as a hydrocarbon solvent or an ether solvent may be used.

The reaction proceeds smoothly within a temperature range of from −78° C. to room temperature.

Now, referring to the reaction, (v), a fluorine-containing α,ω-diisocyanate i.e. a compound of the formula I wherein X is —NCO, is prepared by subjecting the fluorine-containing α,ω-dicarbonyl diazide i.e. the compound of the formula I wherein X is —CON$_3$, to Curtius rearrangement.

The reaction is preferably conducted in a solvent. A solvent which is inert to the reaction, such as a hydrocarbon solvent or an ether solvent can be used.

The reaction proceeds smoothly within a temperature range of from 50 to 150° C.

When the compound of the formula I wherein X is —NCO is prepared by a continuous process of the reactions (iii) to (v), it is preferred to conduct the process continuously without isolating the reaction products of the reactions (iii) and (iv) from the viewpoint of the yield and the efficiently of operation.

Now, the present invention will be described in further detail with reference to Examples and Reference Examples. However, it should be understood that the present invention is by no means restricted by such specific Examples.

REFERENCE EXAMPLE 1

$I(CF_2)_4I + CH_2=CH_2 \rightarrow ICH_2CH_2(CF_2)_4CH_2CH_2I$

Into a 10 ml stainless steel autoclave, 1,4-diiodoperfluorobutane (180 μl, 0.1 mmol) and ethanolamine (12 μl, 0.2 mmol) were charged, and ethylene (10 atm) was sealed in. The mixture was stirred at 100° C. for 3 hours. To the reaction mixture, ethyl ether was added, and octane was introduced as a standard substance. Then, GLC was measured, whereby it was found that 1,8-diiodo-3,3,4,4,5,5,6,6-octafluorooctane was produced in a yield of 78%. Hydrochloric acid was added to the reaction mixture, and the ethyl ether layer was separated. The ether was distilled off, and the product was recrystallized from methanol for isolation and purification of 1,8-diiodo-3,3,4,4,5,5,6,6-octafluorooctance.

IR (KBr) 1195, 1171, 1112, 1064, 722, 512 cm$^{-1}$.

$^1$H-NMR (CDCl$_3$, TMS) δ2.1–3.0 (bm,4H), 3.0–3.6 (bm,4H), $^{19}$F-NMR (CDCl$_3$, CFCl$_3$δ-114.4 (m, 4F), -123.0 (m,4F),

Mass m/e (rel. int.) 510 (M$^+$, 85), 383 (55), 141 (67), 77 (100), 65 (72), 51 (25), 47 (21), 28 (25), 27 (35), Anal. Calcd for C$_8$H$_8$F$_8$I$_2$. C: 18.84, H: 1.58. found C: 18.76, H: 1.42.

REFERENCE EXAMPLES 2 to 16

The reaction was conducted in the same manner as in Reference Example 1. The amounts of 1,4-diiodoperfluorobutane and ethylene used for the reaction, the types and the amounts of the catalyst and the amine used, the reaction temperature, the reaction time and the yield are identified in Table 1.

TABLE 1

| Reference Example No. | I(CF$_2$)$_4$I (mmol) | CH$_2$=CH$_2$ (atm) | Fe(CO)$_5$ (mmol) | NH$_2$CH$_2$CH$_2$OH (mmol) | Temp. (°C.) | Time (hr) | Yield (%) |
| --- | --- | --- | --- | --- | --- | --- | --- |
| 2 | 0.5 | 10 | 0.1 | 0.2 | 80 | 4 | 79 |
| 3 | 1.0 | 10 | 0.1 | 0.2 | 60 | 6 | 81 |
| 4 | 0.5 | 50 | 0.1 | 0.2 | r.t. | 8 | 60 |
| 5 | 0.5 | 10 | 0.05 | 0.1 | 100 | 4 | 76 |
| 6 | 0.5 | 10 | 0.1 | | 100 | 6 | 82 |
| 7 | 0.5 | 10 | 0.05 | 0.05 | 100 | 4 | 79 |
| 8 | 0.5 | 10 | 0.05 | Et$_3$N (0.1) | 100 | 4 | 69 |
| 9 | 0.5 | 10 | 0.05 | Et$_2$NH (0.1) | 100 | 4 | 65 |
| 10 | 0.5 | 10 | 0.05 | Py (0.1) | 100 | 4 | 79 |
| 11 | 0.5 | 10 | Fe$_2$(CO)$_9$ (0.049) | | 100 | 4 | 81 |
| 12 | 0.5 | 10 | Fe$_3$(CO)$_{12}$ (0.032) | | 100 | 4 | 90 |
| 13 | 0.5 | 10 | Fe$_2$(CO)$_9$ (0.04) | 0.16 | 100 | 3 | 65 |
| 14 | 0.5 | 10 | Fe$_3$(CO)$_{12}$ (0.03) | 0.16 | 100 | 3 | 69 |
| 15 | 0.5 | 10 | Co$_2$(CO)$_8$ (0.045) | 0.16 | 100 | 3 | 70 |
| 16 | 0.5 | 10 | Ru$_3$(CO)$_{12}$ (0.025) | 0.16 | 100 | 3 | 60 |

REFERENCE EXAMPLE 17

$I(CF_2)_6I + CH_2=CH_2 \rightarrow ICH_2CH_2(CF_2)_6CH_2CH_2I$

Into a 50 ml autoclave, 1,6-diiodoperfluorohexane (2.58 g, 4.46 mmol) and iron dodecacarbonyl (163 mg, 0.32 mmol) were charged, and ethylene (10 atm) was sealed in. The mixture was reacted at 80° C for 5 hours. To the reaction mixture, hydrochloric acid was added, and the product was extracted with ethyl ether and recrystallized from methanol to obtain 1,10-diiodo-3,3,4,4,5,5,6,6,7,7,8,8-dodecafluorodecane (2.65 g) in a yield of 93%.

$^1$H-NMR (CDCl$_3$,TMS) δ2.3–3.1 (m,4H), 3.1–3.4 (m,4H), $^{19}$F-NMR (CDCl$_3$,CFCl$_3$) δ-114.2 (m,4F), -122.1 (m,4F), 123.0 (m,4F),

IR (KBr) 1215, 1170, 1134, 1062, 688, 512 cm$^{-1}$,

Mass m/e (rel. int.) 610 (M+, 100), 463 (24), 141 (46), 77 (65), 65 (43), 51 (20), 27 (19).

REFERENCE EXAMPLE 18

$I(CF_2)_4I + CH_2=CHCH_3 \longrightarrow$ $$\underset{CH_3}{ICHCH_2}(CF_2)_4\underset{CH_3}{CH_2CHI}$$

Into a 50 ml stainless steel autoclave, 1,4-diiodoperfluorobutane (4.7 g, 10.36 mmol) and Fe$_3$(CO$_{12}$) (0.24 g, 0.48 mmol) were charged, and propylene (1,240 ml, 55.4 mmol) was sealed in. Then, the mixture was reacted at 100° C for 24 hours. To the reaction mixture, an aqueous sodium thiosulfate solution was added, and the mixture was extracted with ethyl ether. The ethyl ether layer was washed with water and then dried over anhydrous magnesium sulfate. The solvent was distilled off under reduced pressure, and the residue wa purified by silica gel column chromatography (developer: hexane) to obtain 3.45 g (yield: 62%) of 2,9-diiodo-4,4,5,5,6,6,7,7-octafluorodecane.

mp 35.0–35.5° C.

Anal. Calcd for C$_{10}$H$_{12}$F$_8$I$_2$. C: 22.33, H: 2.25. found C: 22.46, H: 2.22.

IR (KBr) 1365, 1268, 1208, 1165, 1118, 1032, 868, 715, 502 cm$^{-1}$.

$^1$H-NMR (CDCl$_3$,TMS) δ2.04 (d,J=7Hz,6H), 2.2–3.30 (m,4H), 4.45 (tq,J=7 and 7Hz,2H).

$^{19}$F-NMR (CDCl$_3$,CFCl$_3$) δ-114.2 (m,4F), -124.0 (m,4F),

Mass m/e (rel. int.) 538 (M+, 2), 410 (4), 283 (29), 155 (12), 91 (22), 77 (11), 65 (18), 47 (100), 41 (25).

REFERENCE EXAMPLE 19

$I(CF_2)_6I + CH_2=CHCH_3 \longrightarrow$ $$\underset{CH_3}{ICHCH_2}(CF_2)_6\underset{CH_3}{CH_2CHI}$$

The reaction was conducted in the same manner as in Reference Example 18 except that 1,4-diiodoperfluorobutane in Reference Example 18 was changed to 1,6-diiodoperfluorohexane, whereby 2,11-diiodo- 4,4,5,5,6,6,7,7,8,8,9,9-dodecafluorododecane was obtained in a yield of 89%.

mp 53° C.

Anal. Calcd for $C_{12}H_{12}F_{12}I_2$.

C: 22.59, H: 1.90.

found C: 22.22, H: 1.74.

IR (KBr) 1455, 1368, 1272, 1202, 1170, 1140, 1019, 689, 660, 508 cm$^{-1}$.

$^1$H-NMR (CDCl$_3$,TMS) δ2.04 (d,J=7Hz,6H), 2.30-3.30 (m,4H), 4.45 (tq,J=7 and 7Hz,2H).

$^{19}$F-NMR (CDCl$_3$,CFCl$_3$) δ-114.1 (m,4F), -122.1 (m,4F), -124.0 (m,4F),

Mass m/e (rel. int.) 638 (M+, 1), 384 (15), 91 (9), 65 (12), 47 (100), 43 (41).

EXAMPLE 1

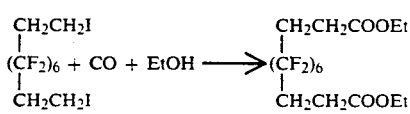

Into a 10 ml stainless steel autoclave, 1,10-diiodo-3,3,4,4,5,5,6,6,7,7,8,8-dodecafluorodocane (0.153 g, 0.25 mmol), Co2(CO)8 (8.5 mg, 0.025 mmol), KF (58 mg, 1 mmol) and ethanol (1 ml) were charged, and CO (50 atm) was sealed in. The mixture was reacted at 100° C. for 24 hours. As an internal standard, nonane (20 μl, 0.112 mmol) was added, and the product was quantitatively analyzed by gas chromatography, whereby it was found that diethyl 4,4,5,5,6,6,7,7,8,8,9,9-dodecafluoro-1,12-dodecanedioate was produced on a yield of 72%. The product was isolated and purified by silica gel column chromatography.

Anal. Calcd for $C_{16}H_{18}F_{12}O_4$. C: 38.26, H: 3.61.

found C: 38.15, H: 3.54.

IR (neat) 1738 cm$^{-1}$ ($\nu$C=O).

$^1$H NMR (CDCl$_3$,TMS) δ1.26 (t,J=7Hz,6H), 2.1-2.9 (m,8H), 4.18 (q,J=7Hz,4H).

$^{19}$F-NMR (CDCl$_3$,CFCl$_3$) δ-115 2 (br,4F), -122.4 (br,4F), -124.1 (br,4F),

Mass m/e (rel. int.) 502 (M+, 16), 457 (100), 429 (99), 402 (21), 129 (26), 123 (22), 77 (24), 55 (48), 45 (20), 29 (93).

EXAMPLES 2 TO 5

The reaction was conducted under the same conditions as in Example 1 except for the catalyst and the base used for the reaction, to obtain diethyl 4,4,5,5,6,6,7,7,8,8,9,9-dodecafluoro-1,12-dodecanedioate. The types and the amounts of the catalyst and base used for the reaction and the yield are shown in Table 2.

TABLE 2

| Example No. | Catalyst (mmol) | Base (mmol) | Yield (%) |
|---|---|---|---|
| 2 | Co2(CO)8 (0.025) | Et3N (0.5) | 54 |
| 3 | (Ph3P)2PdCl2 (0.025) | KF (1) | 50 |
| 4 | (Ph3P)2PdCl2 (0.025) | Et3N (0.5) | 67 |
| 5 | Rh6(CO)16 (0.004) | Et3N (0.5) | 11 |

EXAMPLE 6

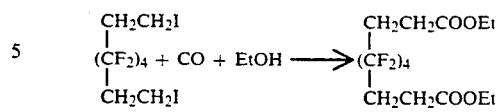

Into a 10 ml stainless steel autoclave, 1,8-diiodo-3,3,4,4,5,5,6,6-octafluorooctane (128 mg, 0.25 mmol), Co2(CO)8 (8.5 mg, 0.0025 mmol), KF (58 mg, 1 mmol) and ethanol (1 ml) were charged, and CO (50 atm) was sealed in. The mixture was reacted at 100° C. for 24 hours. As an internal standard, n-tetradecane (20 μl, 0.077 mmol) was added, and the product was quantitatively analyzed by gas chromatography, whereby it was found that diethyl 4,4,5,5,6,6,7,7-octafluoro-1,10-decanedioate was produced in a yield of 64%. The product was isolated and purified by silica gel column chromatography.

Anal. Calcd for $C_{14}H_{18}F_8O_4$. C: 41.80, H: 4.51.

found C: 41.66, H: 4.58.

IR (neat) 1738 cm$^{-1}$ ($\nu$C=O).

$^1$H-NMR (CDCl$_3$,TMS) δ1.26 (t,J=7Hz,6H), 2.1-2.95 (m,8H), 4.18 (q,J=7Hz,4H).

$^{19}$F-NMR (CDCl$_3$,CFCl$_3$) δ-113.9 (br,4F), -122.7 (br,4F).

Mass m/e (rel. int.) 402 (M+, 6), 357 (60), 329 (31), 284 (5), 55 (53), 45 (16), 29 (100).

EXAMPLES 7 TO 11

The reaction was conducted under the same conditions as in Example 6 except for the catalyst and base used for the reaction, to obtain diethyl 4,4,5,5,6,6,7,7-octafluoro-1,10-decanedioate. The types and the amounts of the catalyst and base used for the reaction and the yield are shown in Table 3.

TABLE 3

| Example No. | Catalyst (mmol) | Base (mmol) | Yield (%) |
|---|---|---|---|
| 7 | Co2(CO)8 (0.025) | Et3N (0.5) | 54 |
| 8 | (Ph3P)2PdCl2 (0.025) | KF (1) | 54 |
| 9 | (Ph3P)2PdCl2 (0.025) | Et3N (0.5) | 64 |
| 10 | Rh6(CO)16 (0.004) | KF (1) | 4 |
| 11 | Rh6(CO)16 (0.004) | Et3N (0.5) | 9 |

EXAMPLE 12

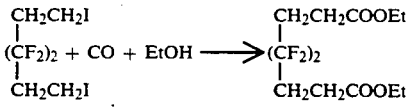

Into a 30 ml stainless steel autoclave, 1,6-diiodo-3,3,4,4-tetrafluorohexane (0.41 g, 1 mmol), Co2(CO)8 (34 mg, 0.1 mmol), KF (0.236 g, 4 mmol) and ethanol (4 ml) were charged, and CO (50 atm) was sealed in. The mixture was reacted at 100° C for 24 hours. After completion of the reaction, the product was extracted with ethyl ether and washed with water. Then, the ethyl ether layer was dried over anhydrous magnesium sulfate. The ethyl ether was distilled off under reduced pressure, and the residue was purified by silica gel column chromatography (developer: chloroform) to obtain 0.233 g (yield: 77%) of diethyl 4,4,5,5-tetrafluoro-1,8-octanedioate.

Anal. Calcd for $C_{12}H_{18}F_4O_4$. C: 47.68, H: 6.00.

found C: 47.40, H: 6.02.

IR (neat) 1740 cm$^{-1}$ ($\nu$C=O).

$^1$H-NMR (CDCl$_3$,TMS) $\delta$1.26 (t,J=7Hz,6H), 2.0-2.8 (m,8H), 4.18 (q,J=7Hz,4H).

$^{19}$F-NMR (CDCl$_3$,CFCl$_3$) $\delta$-137.7 (m,4F).

Mass m/e (rel. int.) 302 (M$^+$, 8), 257 (47), 229 (15), 209 (56), 55 (60), 29 (100).

EXAMPLE 13

The reaction was conducted under the same conditions as in Example 12 except that in Example 12, Co$_2$(CO)$_8$ was changed to (Ph$_3$P)$_2$PdCl$_2$ (70 mg, 0.1 mmol), and KF was changed to Et$_3$N (0.28 ml, 2 mmol). As a result, diethyl 4,4,5,5-tetrafluoro-1,8-octanedioate was obtained in a yield of 86%.

EXAMPLE 14

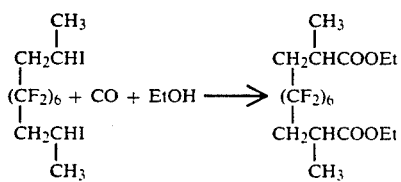

Into a 50 ml stainless steel autoclave, 2,11-diiodo-4,4,5,5,6,6,7,7,8,8,9,9-dodecafluorododecane (0.638 g, 1 mmol), (Ph$_3$P)$_2$PdCl$_2$ (70 mg, 0.1 mmol), KF (0.232 g, 4 mmol) and ethanol (4 ml) were charged, and CO (50 atm) was sealed in. The mixture was reacted at 100° C. for 24 hours. The reaction mixture was extracted with ethyl ether, and the ethyl ether layer was washed with water and then dried over anhydrous magnesium sulfate. The solvent was distilled off under reduced pressure, and the residue was purified by silica gel column chromatography (developer: chloroform) to obtain 0.408 g (yield: 77%) of diethyl 2,11-dimethyl-4,4,5,5,6,6,7,7,8,8,9,9-dodecafluoro-1,12-dodecanedioate.

Anal. Calcd for C$_{18}$H$_{22}$F$_{12}$O$_4$. C: 40.77, H: 4.18.

found C: 40.87, H: 4.10.

IR (neat) 1740 cm$^{-1}$ ($\delta$C=O).

$^1$H-NMR (CDCl$_3$,TMS) $\delta$1.25 (t,J=7Hz,6H), 1.30 (d,J=7Hz,6H), 1.85-3.1 (m,6H), 4.18 (q,J=7Hz,4H).

$^{19}$F NMR (CDCl$_3$,CFCl$_3$) $\delta$-115.3 (br,4F), -123.6 (br,4F), -125.7 (br,4F).

Mass m/e (rel. int.) 530 (M$^+$, 10), 485 (26), 457 (30), 429 (21), 91 (28), 73 (15), 47 (62), 45 (11), 29 (100).

EXAMPLES 15 TO 18

In the same manner as in Example 14, diethyl 2,11-dimethyl-4,4,5,5,6,6,7,7,8,8,9,9-dodecafluoro-1,12-dodecanedioate was obtained. The amount of 2,11-diiodo-4,4,5,5,6,6,7,7,8,8,9,9-dodecafluorododecane used for the reaction, the types and amounts of the catalyst and the base used, the amount of the solvent and the yield are shown in Table 4.

TABLE 4

| Example No. | Substrate (mmol) | Catalyst (mmol) | Base (mmol) | Ethanol (ml) | Yield (%) |
|---|---|---|---|---|---|
| 15 | 1 | Co$_2$(CO)$_8$ (0.1) | KF (4) | 4 | 51 |
| 16 | 0.25 | Rh$_6$(CO)$_{16}$ (0.004) | KF (1) | 1 | 26 |
| 17 | 0.25 | Ru$_3$(CO)$_{12}$ (0.008) | KF (1) | 1 | 33 |
| 18 | 0.25 | (Ph$_3$P)$_2$PtCl$_2$ (0.025) | KF (1) | 1 | 25 |

EXAMPLE 19

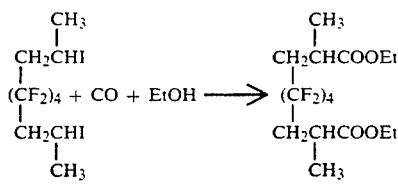

The reaction was conducted under the same conditions as in Example 14 except that 2,11 diiodo-4,4,5,5,6,6,7,7,8,8,9,9-dodecafluorododecane in Example was changed to 2,9-diiodo-4,4,5,5,6,6,7,7-octafluorodecane (0.538 g, 1 mmol), to obtain 0.348 g (yield: 81%) of diethyl 2,9-dimethyl-4,4,5,5,6,6,7,7-octafluoro-1,10-decanedioate.

Anal. Calcd for C$_{16}$H$_{22}$F$_8$O$_4$. C: 44.66, H: 5.15.

found C: 44.38, H: 5.11.

IR (neat) 1740 cm$^{-1}$ ($\nu$C=O).

$^1$H NMR (CDCl$_3$,TMS) $\delta$1.25 (t,J=7Hz,6H), 1.30 (d,J=7Hz,6H) 1.9-3.1 (m,6H), 4.17 (q,J=7Hz,4H).

$^{19}$F-NMR (CDCl$_3$,CFCl$_3$) $\delta$-119.9 (br,4F), -126.1 (br,4F).

Mass m/e (rel. int.) 430 (M$^+$, 14), 385 (36), 357 (36), 269 (24), 91 (35), 47 (34), 29 (100).

EXAMPLES 20 TO 23

In the same manner as in Example 19, diethyl 2,9-dimethyl-4,4,5,5,6,6,7,7-octafluoro-1,10-decanedioate was prepared. The amount of 2,9-diiodo-4,4,5,5,6,6,7,7-octafluorodecane used for the reaction, the types and the amounts of the catalyst and the base used, the amount of the solvent and the yield are shown in Table 5.

TABLE 5

| Example No. | Substrate (mmol) | Catalyst (mmol) | Base (mmol) | Ethanol (ml) | Yield (%) |
|---|---|---|---|---|---|
| 20 | 1 | Co$_2$(CO)$_8$ (0.1) | KF (4) | 4 | 66 |
| 21 | 0.25 | Rh$_6$(CO)$_{16}$ (0.004) | KF (1) | 1 | 37 |
| 22 | 0.25 | Ru$_3$(CO)$_{12}$ (0.008) | KF (1) | 1 | 48 |
| 23 | 0.25 | (Ph$_3$P)$_2$PtCl$_2$ (0.025) | KF (1) | 1 | 48 |

REFERENCE EXAMPLE 20

The measured values of the refractive indices of the fluorine-containing $\alpha,\omega$-diesters obtained in the present invention are shown in Table 6. For the purpose of comparison, the refractive indices of the hydrocarbon diesters having the same number of carbon atoms as the main chains of the dicarboxylic acids obtained in the present invention, are also given. The refractive indices were measured by a refractive index meter manufactured by Atago K. K.

TABLE 6

Refractive indices

| | R<br>\|<br>CH$_2$CHCOOEt<br>\|<br>(CF$_2$)$_n$<br>\|<br>CH$_2$CHCOOEt<br>\|<br>R<br>Refractive index<br>(n$_D^{20}$) | R<br>\|<br>CH$_2$CHCOOEt<br>\|<br>(CH$_2$)$_n$<br>\|<br>CH$_2$CHCOOEt<br>\|<br>R<br>Refractive index<br>(n$_D^{20}$) | Difference in the refractive index (n$_D^{20}$) |
|---|---|---|---|
| n = 2, R = H | 1.4050 | 1.4323 | 0.0273 |
| n = 4, R = H | 1.3880 | 1.4358 | 0.0478 |
| n = 6, R = H | 1.3780 | 1.4402 | 0.0622 |
| n = 4, R = CH$_3$ | 1.3930 | — | — |
| n = 6, R = CH$_3$ | 1.3818 | — | — |

EXAMPLE 24

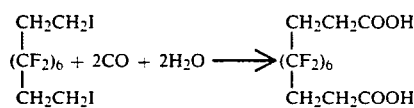

Into a 200 ml stainless steel autoclave, 1,10-diiodo-3,3,4,4,5,5,6,6,7,7,8,8-dodecafluorodecane (14.65 g, 24 mmol), Co$_2$(CO)$_8$ (1.63 g, 4.77 mmol), KF (5.6 g, 96 mmol), water (8.8 ml, 488 mmol) and t-BuOH (80 ml) were charged, and CO (50 atm) was sealed in. The mixture was reacted at 80° C. for 48 hours. Concentrated hydrochloric acid was put into the reaction mixture, and the mixture was extracted with ethyl ether. The ethyl ether layer was washed with water and dried over anhydrous magnesium sulfate. The ethyl ether was distilled off under reduced pressure, and the residue was recrystallized from ethyl ether-hexane to obtain 10.09 g (yield: 94%) of 4,4,5,5,6,6,7,7,8,8,9,9-dodecafluoro-1,12-dodecanedioic acid as white powder.

mp 182° C.

IR (KBr) 3300–2800 cm$^{-1}$ ($v$O—H) 1715 cm$^{-1}$ ($v$ C=O).

Anal. Calcd for C$_{12}$H$_{10}$F$_{12}$O$_4$. C: 32.30, H: 2.26.
found C 32.44, H: 2.29.

$^1$H-NMR (d$_6$-acetone,TMS) δ2.4 (m,4H), 2.7 (m,4H), 9.0 (br,2H).

$^{19}$F-NMR (d$_6$-acetone,CFCl$_3$) δ-114.1 (br,4F), -121.3 (br,4F), -123.2 (br,4F).

Mass m/e (rel. int.) 429 (M$^+$-17,20), 402 (41), 139 (52), 131 (37), 123 (33), 109 (47), 103 (100), 77 (62), 59 (64), 55 (80), 47 (44), 45 (40).

EXAMPLES 25 TO 27

In the same manner as in Example 24, carbon monooxide (50 atm) and water (20 equivalent) were reacted to 1,10-diiodo-3,3,4,4,5,5,6,6,7,7,8,8-dodecafluorodecane as the starting material, under the following conditions, to obtain 4,4,5,5,6,6,7,7,8,8,9,9-dodecafluoro-1,12-dodecanedioic acid. The results are shown in Table 7.

TABLE 7

| Example No. | ICH$_2$CH$_2$(CF$_2$)$_6$CH$_2$CH$_2$I (mmol) | Catalyst (mmol) | Base (mmol) | t-BuOH (ml) | Temp. (°C.) | Time (hr) | Yield of dicarboxylic acid (%) |
|---|---|---|---|---|---|---|---|
| 25 | 3 | Co$_2$(CO)$_8$ (0.3) | KF (12) | 15 | 80 | 63 | 99 |
| 26 | 3 | Co$_2$(CO)$_8$ (0.3) | KF (12) | 10 | 80 | 48 | 95 |
| 27 | 1 | PdCl$_2$(PPh$_3$)$_2$ (0.11) | KF (4) | 5 | 80 | 48 | 97 |

EXAMPLE 28

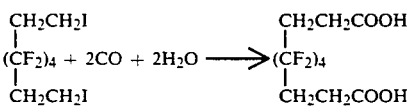

The reaction was conducted under the same conditions as in Example 24 except that the 1,10-diiodo-3,3,4,4,5,5,6,6,7,7,8,8-dodecafluorodecane in Example 24 was changed to 1,8-diiodo-3,3,4,4,5,5,6,6-octafluorooctane (12.24 g, 24 mmol), to obtain 6.65 g (yield: 80%) of 4,4,5,5,6,6,7,7-octafluoro-1,10-decanedioic acid as white powder.

mp 187–187.5° C.

IR (KBr) 3300–2800 cm$^{-1}$ (δO—H) 1720 cm$^{-1}$ ($v$C=O).

Anal. Calcd for C$_{10}$H$_{10}$F$_8$O$_4$. C: 34.70, H: 2.91.
found C: 34.75, H: 2.75.

$^1$H-NMR (d$_6$-acetone,TMS) δ2.51 (m,4H), 2.66 (m,4H), 11.0 (br,2H).

$^{19}$F-NMR (d$_6$-aeetone,CFCl$_3$) δ-114.4 (br,4F), -123.3 (br,4F).

Mass m/e (rel. int.) 329 (M$^+$-17,11), 302 (8), 123 (23), 109 (31), 103 (86), 77 (56), 73 (41), 59 (48), 55 (100), 47 (51), 45 (41).

EXAMPLES 29 AND 30

In the same manner as in Example 28, carbon monooxide (50 atm) and water (20 equivalents) were reacted to 1,8-diiodo-3,3,4,4,5,5,6,6-octafluorooctane as a starting material, under the following conditions, to obtain 4,4,5,5,6,6,7,7-octafluoro-1,10-decanedioic acid. The results are shown in Table 8.

TABLE 8

| Example No. | ICH$_2$CH$_2$(CF$_2$)$_4$CH$_2$CH$_2$I (mmol) | Catalyst (mmol) | Base (mmol) | t-BuOH (ml) | Temp. (°C.) | Time (hr) | Yield of dicarboxylic acid (%) |
|---|---|---|---|---|---|---|---|
| 29 | 3 | Co$_2$(CO)$_8$ (0.6) | KF (12) | 15 | 80 | 48 | 96 |
| 30 | 1 | PdCl$_2$(PPh$_3$)$_2$ (0.1) | KF (4) | 5 | 80 | 48 | 93 |

EXAMPLE 31

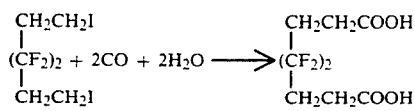

Into a 20 ml stainless steel autoclave, 1,6-diiodo-3,3,4,4-tetrafluorohexane (0.41 g, 1 mmol), Co$_2$(CO)$_8$ (33 mg, 0.1 mmol), KF (0.24 g, 4 mmol), water (0.36 ml, 20 mmol) and t-BuOH (3 ml) were charged, and CO (50 atm) was sealed in. The mixture was reacted at 80° C for 48 hours. A 3N hydrochloric acid aqueous solution was put to the reaction mixture, and the mixture was extracted with ethyl ether. The ethyl ether layer was washed with water and dried over anhydrous magnesium sulfate. The ethyl ether was distilled off under reduced pressure, and the residue was recrystallized from ethyl ether-hexane to obtain 0.24 g (yield: 97%) of 4,4,5,5-tetrafluoro-1,8-octanedioic acid as white powder.

mp 204° C.

IR (KBr) 3450-3200 cm$^{-1}$ ($\nu$O—H) 1710 cm$^{-1}$ ($\nu$C=O).

$^1$H-NMR (d$_6$-acetone,TMS) $\delta$2.1-3.0 (m,8H).

$^{19}$F-NMR (d$_6$-aCetone,CFCl$_3$) $\delta$-115.9 (br,4F).

Mass m/e (rel. int.) 229 (M$^+$-17,7), 208 (10), 161 (10), 123 (37), 103 (100), 77 (40), 73 (40), 60 (58), 55 (78), 47 (47), 42 (42), 28 (34).

EXAMPLE 32

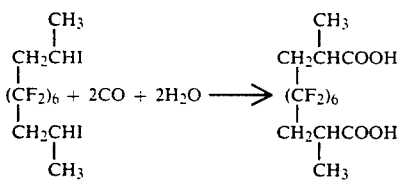

The reaction was conducted under the same conditions as in Example 31 except that the 1,6-diiodo-3,3,4,4-tetrafluorohexane in Example 31 was changed to 2,11-diiodo-4,4,5,5,6,6,7,7,8,8,9,9-dodecafluorodecane (0.47 g, 1 mmol), and the amount of t-BuOH was changed to 5 ml, whereby 2,11-dimethyl-4,4,5,5,6,6,7,7,8,8,9,9-dodecafluoro-1,12-dodecanedioic acid was obtained in a yield of 67%.

mp 149.5-151° C.

Anal. Calcd for C$_{14}$H$_{14}$F$_{12}$O$_4$. C: 35.46, H: 2.98.
found C: 35.56, H: 2.99.

IR (KBr) 3200-2800 cm$^{-1}$ ($\delta$O—H) 1710 cm$^{-1}$ ($\delta$C=O).

$^1$H-NMR (d$_6$-acetone,TMS) $\delta$1.33 (d,J=8Hz,6H), 1.6-3.1 (m,6H), 11.0 (br,2H).

$^{19}$F-NMR (d$_6$-acetone,CFCl$_3$) $\delta$-113.2 (br,4F), -121.6 (br,4F), -123.7 (br,4F).

Mass m/e (rel. int.) 457 (M$^+$-17,2), 430 (14), 163 (21), 153 (22), 133 (33), 121 (32), 91 (60), 87 (30), 73 (75), 47 (100), 45 (37), 41 (51), 28 (34).

EXAMPLE 33

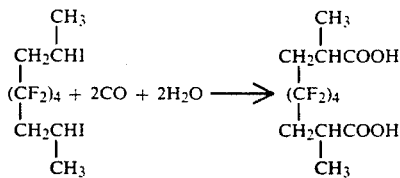

The reaction was conducted under the same conditions as in Example 31 except that the 1,6-diiodo-3,3,4,4-tetrafluorohexane in Example 31 was changed to 2,9-diiodo-4,4,5,5,6,6,7,7-octafluorodecane (0.37 g, 1 mmol). As a result, 2,9-dimethyl-4,4,5,5,6,6,7,7-octafluoro-1,10-decanedioic acid was obtained in a yield of 69%.

mp 166-168° C.

Anal. Calcd for C$_{12}$H$_{14}$F$_8$O$_4$. C: 38.51, H: 3.77.
found C: 38.38, H: 3.69.

IR (KBr) 3200-2800 cm$^{-1}$ ($\delta$O—H) 1710 cm$^{-1}$ ($\nu$C=O).

$^1$H-NMR (d$_6$-acetone,TMS) $\delta$1.33 (d,J=8Hz,6H), 1.6-3.1 (m,6H), 10.8 (br,2H).

$^{19}$F-NMR (d$_6$-aCetone,CFCl$_3$) $\delta$-113.4 (br,4F), -123.7 (br,4F).

Mass m/e (rel. int.) 357 (M$^+$-17,3), 330 (7), 153 (27), 137 (17), 111 (23), 103 (16), 99 (17), 95 (18), 91 (67), 89 (52), 87 (34), 77 (24), 73 (68), 69 (41), 61 (27), 59 (22), 47 (65), 45 (45), 28 (60), 18 (100).

REFERENCE EXAMPLE 21

As one of the physical properties of the fluorine-containing $\alpha,\omega$-dicarboxylic acids obtained by the present invention, the contact angle with water was measured. The measuring method was such that a dicarboxylic acid was finely pulverized in an agate mortar and pressed under a pressure of 300 kg/cm$^2$ under reduced pressure to obtain a sample plate. A water drop was dropped thereon, and the contact angle with the water was immediately measured by the contact angle measuring apparatus (manufactured by Erma). For the purpose of comparison, the contact angles of the hydrocarbon $\alpha,\omega$-dicarboxylic acids having the same number of carbon atoms as the fluorine-containing $\alpha,\omega$-dicarboxylic acids obtained by the present invention, are given. The results are shown in Table 9.

TABLE 9

| | Contact angle with water | | |
|---|---|---|---|
| | R<br>\|<br>CH$_2$CHCOOH<br>\|<br>(CF$_2$)$_n$<br>\|<br>CH$_2$CHCOOH<br>\|<br>R<br>Contact angle | R<br>\|<br>CH$_2$CHCOOH<br>\|<br>(CH$_2$)$_n$<br>\|<br>CH$_2$CHCOOH<br>\|<br>R<br>Contact angle | Difference in contact angle |
| n = 2, R = H | 53.0°* | 40.0°* | 13.0° |
| n = 4, R = H | 65.0° | 39.8°* | 25.2° |
| n = 6, R = H | 69.5° | 43.2°* | 26.3° |
| n = 4, R = CH$_3$ | 63.3° | — | — |

*In 3 hours, the water drop was completely absorbed.

REFERENCE EXAMPLE 22

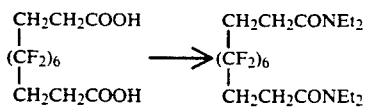

4,4,5,5,6,6,7,7,8,8,9,9-dodecafluoro-1,12-dodecanedioic acid was refluxed for 2 hours in thionyl chloride (2 ml) under an argon atmosphere. Excess thionyl chloride was distilled off under reduced pressure, and then ethyl ether (4 ml) was added and the residue was dissolved. Then, diethylamine (1.24 ml, 12 mmol) was gradually dropwise added thereto. The mixture was stirred at room temperature for 30 minutes. Then, the reaction solution was extracted with ethyl ether. The ethyl ether layer was washed with water and then dried over anhydrous magnesium sulfate. The solvent was distilled off, and the residue was purified by silica gel column chromatography (developer: chloroform/ethyl acetate =1/1) to obtain 0.84 g (yield: 75%) of 4,4,5,5,6,6,7,7,8,8,9,9-dodecafluoro-N,N,N′,N′-tetraethyl-1,12-dodecanediamide.

IR (neat) 1642 cm$^{-1}$ ($\nu$C=O).

$^1$H-NMR (CDCl$_3$,TMS) $\delta$1.10 (t,J=7Hz,6H), 1.18 (t,J=7Hz,6H), 2.1–3.0 (m,8H), 3.32 (q,J=7Hz,4H), 3.40 (q,J=7Hz,4H).

$^{19}$F-NMR (CDCl$_3$,CFCl$_3$) $\delta$-114.8 (br,4F), -122.2 (br,4F), -124.1 (br,4F).

REFERENCE EXAMPLE 23

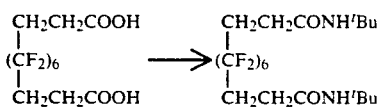

The operation was conducted in the same manner as in Reference Example 22 except that the diethylamine in Reference Example 22 was changed to t butylamine. As a result, 4,4,5,5,6,6,7,7,8,8,8,9,9 dodecafluoro-N,N′-di-t-butyl-1,12-dodecanediamide was obtained in a yield of 77%.

IR (KBr) 3340 cm$^{-1}$ ($\nu$N—H) 1650 cm$^{-1}$ ($\nu$C=O).

$^1$H-NMR (CDCl$_3$,TMS) $\delta$1.35 (s,18H), 2.1–2.7 (m,8H), 5.25 (br,2H).

$^{19}$F-NMR (CDCl$_3$,CFCl$_3$) $\delta$-114.8 (br,4F), -122.3 (br,4F), -124.1 (br,4F).

EXAMPLE 34

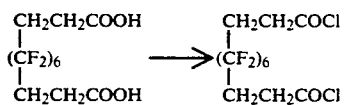

4,4,5,5,6,6,7,7,8,8,9,9-dodecafluoro-1,12-dodecanedioic acid (0.892 g, 2 mmol) was refluxed for 2 hours in thionyl chloride (2 ml) under an argon atmosphere. Excess thionyl chloride was distilled off under reduced pressure to obtain 4,4,5,5,6,6,7,7,8,8,9,9-dodecafluoro-1,12-dodecanedioyl dichloride.

$^1$H-NMR (CDCl$_3$,TMS) $\delta$2.45 (4H,tt,J=18 and 7Hz), 3.24 (4H,t,J=7Hz).

IR (KBr) 1785 cm$^{-1}$ ($\nu$CO).

EXAMPLE 35

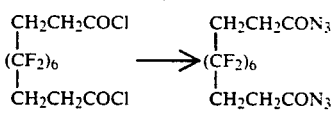

The 4,4,5,5,6,6,7,7,8,8,9,9-dodecafluoro-1,12-dodecanedioyl dichloride obtained in Example 34 was dissolved in toluene (2 ml) and cooled with ice. To this solution, a mixture of a toluene solution of HN3 (1.3M, 3.1 ml, 4 mmol) and pyridine (0.33 ml, 4 mmol) was gradually added and stirred for 15 minutes under cooling with ice. Formed pyridine hydrochloride was removed by filtration and washed with toluene. From the filtrate, excess HN3 was removed by an aspirater to obtain a toluene solution of 4,4,5,5,6,6,7,7,8,8,9,9-dodecafluoro-1,12-dodecanedioyl diazide.

IR (KBr filed cell, toluene) 2145 cm$^{-1}$ ($\nu$N$_3$) 1722 cm$-1$ ($\nu$CO).

EXAMPLE 36

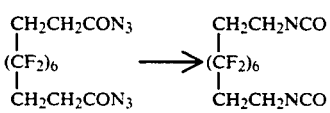

The toluene solution of 4,4,5,5,6,6,7,7,8,8,9,9-dodecafluoro-1,12-dodecanedioyl diazide obtained in Example 35 was stirred at 95° C. for 1 hour. The solvent was distilled off under reduced pressure to obtain 3,3,4,4,5,5,6,6,7,7,8,8-dodecafluoro-1,10-diisocyanatedecane in an overall yield of 64% (0.565 g) from Example 34.

Anal. Calcd for C$_{12}$H$_8$F$_{12}$N$_2$O$_2$. C: 32.74, H: 1.83, N: 6.36.

found C: 32.74, H: 1.83, N: 6.56.

IR (neat) 2270 cm$^{-1}$ ($\nu$ NCO) 1190 cm$^{-1}$ ($\nu$C—F).

$^1$H-NMR (CDCl$_3$,TMS) $\delta$2.40 (4H,tt,J=18 and 7Hz), 3.65 (4H,t,J=7Hz).

$^{19}$F-NMR (CDCl$_3$,CFCl$_3$) $\delta$-114.7 (br,4F), -122.2 (br,4F), -124.1 (br,4F).

Mass m/e (rel. int.) 441 (M$^+$+1), 412, 385 (3), 56 (100).

EXAMPLE 37

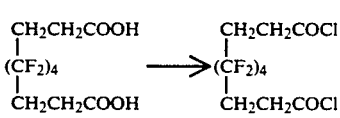

4,5,5,6,6,7,7-octafluoro-1,10-decanedioic acid (1.02 g, 2.94 mmol) was refluxed for 2 hours in thionyl chloride (3 ml) in an argon atmosphere. Excess thionyl chloride was distilled off under reduced pressure to obtain 4,4,5,5,6,6,7,7-octafluoro-1,10-decanedioyl dichloride.

$^1$H-NMR (CDCl$_3$,TMS) $\delta$2.53 (4H,tt,J=18 and 7Hz), 3.24 (4H,t,J=7Hz).

IR (KBr) 1795 cm$^{-1}$ ($\delta$CO).

EXAMPLE 38

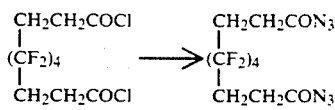

The 4,4,5,5,6,6,7,7-octafluoro-1,10-decanedioyl dichloride obtained in Example 37 was dissolved in toluene (3 ml) and then cooled with ice. To this solution, a mixture comprising a toluene solution of $HN_3$ (1.3M, 4.6 ml, 5.98 mmol) and pyridine (0.49 ml, 6.05 mmol) was gradually added and stirred for 15 minutes under cooling with ice. Formed pyridine hydrochloride was removed by filtration and washed with toluene. Excess $HN_3$ was removed from the filtrate by an aspirater to obtain a toluene solution of 4,4,5,5,6,6,7,7-octafluoro-1,10-decanedioyl diazide.

IR (KBr fixed cell, toluene) 2150 cm$^{-1}$ ($\nu N_3$) 1722 cm$^{-1}$ ($\nu CO$).

EXAMPLE 39

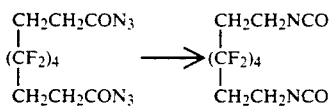

The toluene solution of 4,4,5,5,6,6,7,7-octafluoro-1,10-decanedioyl diazide obtained in Example 38 was stirred at 95° C. for 1 hour. The solvent was removed under reduced pressure to obtain 3,3,4,4,5,5,6,6-octafluoro-1,8-diisocyanateoctane in an overall yield of 87% (0.867 g) from Example 37.

IR (neat) 2280 cm$^{-1}$ ($\nu NCO$) 1170 cm$^{-1}$ ($\nu C-F$).

$^1$H-NMR (CDCl$_3$,TMS) δ2.41 (4H,tt,J=18 and 7Hz), 3.66 (4H,t,J=7Hz).

$^{19}$F-NMR (CDCl$_3$,CFCl$_3$) δ-114.9 (br,4F), -124.1 (br,4F).

Mass m/e (rel. int.) 341 (M$^+$+1), 284 (2), 56 (100).

EXAMPLE 40

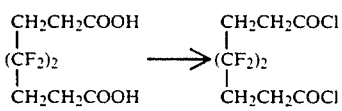

4,4,5,5-tetrafluoro-1,8-octanedioic acid (0.537 g, 2.18 mmol) was refluxed for 2 hours in thionyl chloride (2.5 ml) under an argon atmosphere. Excess thionyl chloride was removed under reduced pressure to obtain 4,4,5,5-tetrafluoro-1,8-octanedioyl dichloride.

$^1$H-NMR (CDCl$_3$,TMS) δ2.48 (4H,tt,J=18 and 7Hz) 3.22 (4H,t,J=7Hz).

IR (KBr) 1790 cm$^{-1}$ ($\nu CO$).

EXAMPLE 41

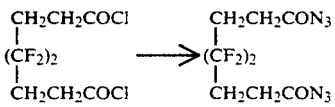

The 4,4,5,5-tetrafluoro-1,8-octanedioyl dichloride obtained in Example 40 was dissolved in toluene (2.5 ml) and cooled with ice. To this solution, a mixture comprising a toluene solution of $HN_3$ (1.3M, 3.4 ml, 4.42 mmol) and pyridine (0.36 ml, 4.45 mmol) was gradually added and stirred for 15 minutes under cooling with ice. Formed pyridine hydrochloride was removed by filtration and washed with toluene. Excess $HN_3$ was removed from the filtrate by an aspirater to obtain a toluene solution of 4,4,5,5-tetrafluoro-1,8-octanedioyl diazide.

IR (KBr fixed cell, toluene) 2130 cm$^{-1}$ ($\nu N_3$) 1722 cm$^{-1}$ ($\nu CO$).

EXAMPLE 42

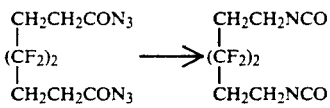

The toluene solution of 4,4,5,5-tetrafluoro-1,8-octanedioyl diazide obtained in Example 41 was stirred at 95° C. for 1 hour. The solvent was distilled off under reduced pressure to obtain 3,3,4,4-tetrafluoro-1,6-diisocyanatehexane in an overall yield of 78% (0.416 g) from Example 40.

IR (neat) 2275 cm$^{-1}$ ($\nu NCO$) 1170 cm$^{-1}$ ($\nu C-F$).

$^1$H-NMR (CDCl$_3$,TMS) δ2.37 (4H,tt,J=18 and 7Hz), 3.64 (4H,t,J=7Hz).

$^{19}$F-NMR (CDCl$_3$,CFCl$_3$) δ-115.2 (br,4F).

Mass m/e (rel. int.) 241 (M$^+$+1), 184 (16), 56 (100).

EXAMPLE 43

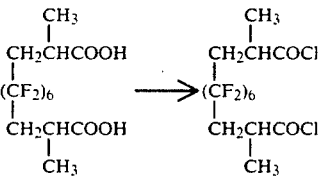

2,11-dimethyl-4,4,5,5,6,6,7,7,8,8,9,9-dodecafluoro-1,12-dodecanedioic acid (0.192 g, 0.4 mmol) was refluxed for 1 hour in thionyl chloride (2 ml) under an argon atmosphere. Excess thionyl chloride was distilled off under reduced pressure to obtain 2,11-dimethyl-4,4,5,5,6,6,7,7,8,8,9,9-dodecafluoro-1,12-dodecanedioyl dichloride quantitatively.

$^1$H-NMR (CDCl$_3$,TMS) δ1.49 (6H,d,J=7.2Hz), 2.17 (2H,m), 2.79 (2H,m), 3.32 (2H,ddq,J=5,2, 7.2, and 7.2Hz).

IR (neat) 1790 cm$^{-1}$ ($\nu CO$).

EXAMPLE 44

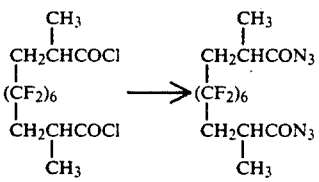

The 2,11-dimethyl-4,4,5,5,6,6,7,7,8,8,9,9-dodecafluoro-1,12-dodecanedioyl dichloride obtained in Example 43 was dissolved in toluene (2 ml) and then cooled with ice. To this solution, a mixture comprising a toluene solution of $HN_3$ (1.3M, 0.6 ml, 0.78 mmol) and pyridine (63 μl, 0.78 mmol) was gradually added and stirred for 15 minutes under cooling with ice. Formed pyridine hydrochloride was removed by filtration and washed with toluene. Excess HN₃ was removed from the filtrate by an aspirater to obtain a toluene solution of 2,11-dimethyl-4,4,5,5,6,6,7,7,8,8,9,9-dodecafluoro-1,12-dodecanedioyl diazide.

IR (KBr fixed cell, toluene) 2148 cm⁻¹ (νN₃) 1720 cm⁻¹ (νCO).

EXAMPLE 45

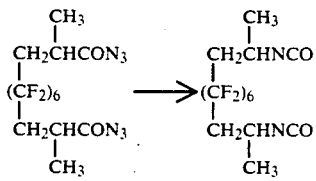

The toluene solution of 2,11-dimethyl-4,4,5,5,6,6,7,7,8,8,9,9-dodecafluoro-1,12-dodecanedioyl diazide obtained in Example 44 was stirred at under heating at 95° C. for 1 hour. The solvent was removed under reduced pressure to obtain 4,4,5,5,6,6,7,7,8,8,9,9-dodecafluoro-2,11-diisocyanatedodecane in an overall yield of 92% (0.172 g) from Example 43.

IR (neat) 2280 cm⁻¹ (νNCO) 1190 cm⁻¹ (νC—F).

¹H-NMR (CDCl₃,TMS) δ1.45 (6H,d,J=7Hz), 2.3 (4H,m), 4.12 (2H,m).

¹⁹F-NMR (CDCl₃,CFCl₃),δ-114.3 (4F,br), -122.1 (4F,br), -124.2 (4F,br).

Mass m/e (rel. int.) 469 (M⁺+1), 468 (M⁺), 390, 70 (100), 56 (18), 42 (26).

We claim:

1. A fluorine-containing α,ω-bifunctional compound having the formula:

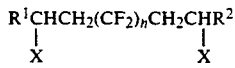

wherein each of R¹ and R² independently is an alkyl group having 1 to 10 carbon atoms or an aralkyl group having 7 to 10 carbon atoms; X is —COOH, —COOR³ or —COY, wherein R³ is an alkyl group having 1 to 5 carbon atoms and Y is a halogen atom; and n is an integer of at least 1.

* * * * *